United States Patent
Rubsamen et al.

[11] Patent Number: 5,829,436
[45] Date of Patent: Nov. 3, 1998

[54] VENTILATION IMAGING USING A FINE PARTICLE AEROSOL GENERATOR

[75] Inventors: Reid M. Rubsamen, Berkeley; Stephen J. Farr, Orinda, both of Calif.; Fred Silverstein, Seattle, Wash.

[73] Assignee: Aradigm Corporation, Hayward, Calif.

[21] Appl. No.: 789,551

[22] Filed: Jan. 27, 1997

Related U.S. Application Data

[63] Continuation-in-part of Ser. No. 597,089, Feb. 5, 1996, abandoned.

[51] Int. Cl.$^6$ .................................................. A61M 11/00
[52] U.S. Cl. ............................... 128/200.14; 128/203.12; 128/200.22
[58] Field of Search ..................... 128/200.14, 200.23, 128/203.12, 204.23, 200.22

[56] References Cited

U.S. PATENT DOCUMENTS

| | | |
|---|---|---|
| 3,812,854 | 5/1974 | Michaels et al. . |
| 5,064,634 | 11/1991 | Burch ........................................ 424/1.1 |
| 5,394,866 | 3/1995 | Ritson et al. . |
| 5,404,871 | 4/1995 | Goodman et al. . |
| 5,450,336 | 9/1995 | Rubsamen et al. . |
| 5,497,763 | 3/1996 | Lloyd et al. ....................... 128/200.14 |
| 5,497,944 | 3/1996 | Weston et al. . |
| 5,522,385 | 6/1996 | Lloyd et al. ....................... 128/203.26 |

FOREIGN PATENT DOCUMENTS

| | | |
|---|---|---|
| 0 358 002 A2 | 3/1990 | European Pat. Off. . |
| 0 430 566 A2 | 6/1991 | European Pat. Off. . |
| 2673142 | 8/1992 | France . |
| 2 255 918 | 11/1992 | United Kingdom . |
| 2 256 805 | 12/1992 | United Kingdom . |
| WO 92/07599 | 5/1992 | WIPO . |
| WO 92/15353 | 9/1992 | WIPO . |

OTHER PUBLICATIONS

Newman S.P. et al., "How should a pressurized β–adrenergic bronchodilator be inhaled?", (1981) *Ear. J. Res. Dis* 62:3–20.

Lowe, V.F. and Sostman, H., "Pulmonary embolism," in: *Nuclear Medicine in Clinical Diagnosis and Treatment*, 1994, I.P.C. Murray and P.J. Ell (eds), Churchill Livingston, vol. 1, pp. 29–46.

Baker, R.J., "Basic Science: radio chemistry," in: *Nuclear Medicine in Clinical Diagnosis and Treatment*, 1994 I.P.C. Murray and P.J. Ell (eds), vol. 2, pp. 347–356.

*An Atlas of Clinical Nuclear Medicine*, Second Edition, 1994, Fogelman et al. (eds), Published by Mosby/Martin Dunitz, England, pp. 521–575.

M.M. Nieminen et al., "Aerosol deposition in automatic dosimeter nebulization", Eur. J. Respir. Dis. (1987) 71, 145–152.

*Primary Examiner*—Aaron J. Lewis
*Attorney, Agent, or Firm*—Bozicevic & Reed LLP; Karl Bozicevic, Esq.

[57] ABSTRACT

A method of diagnosing a patient is carried out by delivering an aerosolized dose of a radioactive formulation to a patient and making a ventilation image of radioactive material deposited in the lung. This image is compared with a separately generated image (perfusion image) taken after injecting radiolabled particles into the pulmonary arterial circulation. Devices, packaging and methodology for creating aerosols are provided which allow for efficient and repeatable delivery of radioaerosols to the lungs of a patient. Devices may be plug-in units or hand-held, self-contained units which are automatically actuated at the same release point in a patient's inspiratory flow cycle. The device is loaded with a container of a radioactive formulation such as $^{99m}$Tc-labelled diethylene-triamine pentaacetic acid (DTPA). Actuation of the device forces the radioactive formulation through a porous membrane of the container which membrane has pores having a diameter in the range of about 0.25 to 6.0 microns. The container includes radioactive shielding in the form of a lead coating and/or a lead surrounding packet. The porous membrane is positioned in alignment with a surface of a channel through which a patient inhales air.

7 Claims, 4 Drawing Sheets

VENTILATION IMAGING USING A FINE PARTICLE AEROSOL GENERATOR

CROSS-REFERENCE

This application is a continuation-in-part of application Ser. No. 08/597,089, filed Feb. 5, 1996, now abandoned, which application is incorporated herein by reference in its entirety and to which application is claimed priority under 35 USC §120.

FIELD OF THE INVENTION

This invention relates generally to the field of nuclear medicine. More specifically, the invention relates to methodology which uses a radioactive formulation in diagnosing the patient such as to determine the existence of lung and circulatory system abnormalities, including pulmonary embolisms.

BACKGROUND OF THE INVENTION

Nuclear imaging involves introducing radioactive material into a patient, and, more specifically, into a particular tissue or tissues of that patient. After the radioactive material has been introduced, an image can be created based on the radioactive quanta emitted by the material when those particle strike a recording media, (e.g., an electronic sensory array) which is sensitive to the radioactive emissions. Images recorded electronically can be displayed on a monitor and/or transferred to film and printed for a permanent record. The process can provide life saving information. For example, tens of thousands of individuals in the United States die each year from pulmonary embolisms (PE). Detecting and diagnosing pulmonary embolisms is particularly difficult in that it often presents nonspecific clinical manifestations caused by the migration of blood clots in the deep veins of the legs (DVP) proceeding through the central venous system and into the pulmonary circulation via the right side of the heart.

A clot within the pulmonary circulation results in inadequate gas exchange between the blood and the lungs, which, if sufficiently massive, can be fatal. In order to diagnose pulmonary embolism a caretaker may carry out pulmonary arterial angiography. This invasive procedure involves introducing a radiopaque dye into the pulmonary artery via percutaneous placement of a catheter into the right ventricle and through the pulmonic valve.

Radiographs taken subsequent to the injection of dye through the catheter can be used to visualize perfusion defects associated with a pulmonary embolism.

In that pulmonary angiography is invasive and time consuming, it is not typically the first test used to rule out pulmonary embolisms in patients presenting clinical signs and systems consistent with pulmonary embolism. Nuclear imaging methodology allows a ventilation-perfusion scan to be used as a screen diagnostic procedure for early evaluation of patients suspected of having a pulmonary embolism.

Ventilation/perfusion scintigraphy is carried out by producing two separate images and comparing the images. In general, a ventilation scan, or V-scan, is carried out first in order to maximize the quality of the study. In order to create a V-scan it is necessary to create an outline of the ventilated regions of the lung. This is done by having the patient inhale a radioactive gas or aerosol. After inhalation an image can be created of the ventilated areas of the lung where the radioactive material has been deposited using a gamma camera. In order for the V-scan image to be useful, the radioactive material must penetrate deep into the lungs and deposit on all ventilated areas of the lungs. Unless the radioactive material reaches and uniformly deposits throughout the lung alveoli, the tests results will be compromised. The compromise is created when an incomplete V-scan image is used as the base for showing the outline of the lung, which outline is compared with the Q-scan in order to determine if all areas of the lung are being supplied with blood.

There are several types of radiopharmaceuticals which are used to create a V-scan image, which include $^{81m}$Kr, $^{133}$Xe, and $^{99m}$Tc-labelled diethylene triamine pentaacetic acid (DTPA). When DTPA is used it is used in the form of an aerosol delivered by a nebulizer. Another more recently developed material is referred to as Technegas, which is produced by heating $^{99m}$Tc pertechnetate in a graphite crucible by means of an electric current, and in pure argon atmosphere. When the temperature reaches 2400° C., $^{99m}$Tc radioactivity is volatilized in association with carbon from the crucible in the form of a microaerosol. The resulting material is not particularly stable as it undergoes coalescence and deposition on the sides of the containing vessel. Accordingly, it must be administered to the patient within ten minutes after generation.

The second image necessary in order to carry out ventilation-perfusion centograph is the perfusion scan or Q-scan. The goal of the Q-scan is to produce an image of the pulmonary arterial circulation. This image will allow for a direct comparison with the V-scan, which will in turn allow for the detection of mismatches between the V-scan and Q-scan. Mismatches of particular types are indicative of the presence of a pulmonary embolism. Particularly, when the V-scan demonstrates that air is reaching a particular area of the lung and the Q-scan shows that no blood is reaching that area of the lung, there is a likelihood of a pulmonary embolism.

In order to create a Q-scan a radioactive material such $^{99m}$Tc macroaggregated albumin (MAA) can be injected into the peripheral venous circulation. After injection an image is created using a gamma camera, which includes an electronic sensor array capable of detecting the radioactive particles emitted. The reliability of the diagnosis is based on the V/T mismatch analysis. This mismatch analysis is often highly dependent on the clarity and reliability of the V-scan which can be compromised for a variety of reasons.

Ventilation images which are created using a radioactive gas are generally preferred in terms of the results obtained. However, radioactive gas is expensive, difficult to handle and use, has a short half life and is often unavailable. A radioactive aerosol is more desirable in terms of its convenience of use, lower expense, and greater availability. However, the quality of the images obtained are generally not as good as that obtained using radioactive gas. The present invention endeavors to provide high quality images in a convenient, inexpensive, readily available manner.

SUMMARY OF THE INVENTION

A method of diagnosing a patient is disclosed, which method comprises creating an aerosolized dose of a formulation containing tagged material such as a radioactive material by moving the formulation through a porous membrane. The aerosol created is inhaled into the peripheral areas of the lungs of a patient and allowed to migrate from lung tissue into the circulatory system of the patient. At a predetermined time following inhalation a measurement is made of the amount of radioactive material and the measured amount is compared with a standard. By making the comparison it is possible to deduce the likelihood of a pulmonary embolism. If the amount measured is a predetermined amount or more below a standard the likelihood of pulmonary embolism can be deduced in that radioactive aerosol delivered to the lung has not been brought into the circulatory system because at least some portion of the lung which is ventilated is not being perfused due to an embolism. More specifically, the tagged or radioactive material has been delivered to ventilated areas of the lung which areas are being perfused due to an embolism. Thus the tagged material remains in the lungs and can not be moved into the circulatory system and detected there.

When a likelihood of an embolism has been deduced a second formulation of radioactive material is aerosolized (preferably by moving it through a porous membrane) and inhaled into the lung. The second formulation is designed for being deposited in the lung and not to quickly migrate into the circulatory system. After the radioactive material is deposited on lung tissue the patient is brought into contact with a medium which is sensitive to radiation emitted by the radioactive material. The exposed medium is processed to create an image of all areas of the lung which are being ventilated. When all areas are ventilated such provides a further indication of pulmonary embolism when the initial readings of radioactive material in the circulatory system were substantially decreased. The detection of decreased radioactivity in the circulatory system is caused when radioactive material is delivered to, for example, fully ventilated lungs which are not fully profused thereby providing no means for the radioactive material deposited on the lung to reach the circulatory system. The degree to which areas of the lung are not ventilated can be related to the amount of decrease of the radioactive material in the circulatory system in order to discount the likelihood of a pulmonary embolism. Patients who have a pulmonary embolism are substantially more likely to have a recurrence of pulmonary embolism as compared with the likelihood of an embolism occurring in an individual who has not had a prior embolism. Accordingly, the present invention is particularly valuable in rediagnosing a pulmonary embolism in a patient with a prior pulmonary embolism which patient had been subjected to a measurement (to provide a standard for comparison) via the present invention at the time of the prior pulmonary embolism. More specifically, the process is carried out by instructing the patient to inhale a formulation of aerosolized radioactive material. The inhaled material is allowed to migrate into the circulatory system. After a given period of time (e.g., five minutes) a measurement is made of the amount of radioactive material in the patient's circulatory system. If the same patient presents symptoms at a later time (e.g., one year thereafter) the same procedure is followed and the earlier measurement compared with the current measurement in order to determine if a further pulmonary embolism has occurred. Further, repeated measurements can be made on the same patient over a period of hours, days or weeks in order to determine if treatment is effective in dissolving any clot and reestablishing circulation.

An important object of the invention is to provide a method of diagnosing pulmonary embolisms by delivering a material tagged with a detectable label such as a radioactive material to a patient by aerosol, measuring the amount of material in a patient's circulatory system after a given point of time by detecting the tag and comparing that measurement to a standard in order to deduce the likelihood of embolism based on the degree of difference between the measured amount in the standard.

Another object of the invention is to provide a method of diagnosing a patient by forcing a radiolabled formulation through a nozzle which creates particles having a diameter in the range of 1 to 10 microns, creating an image of the particles deposited on the lungs (ventilation image) and comparing the ventilation image with a perfusion image taken after injecting a radiolabled formulation into the pulmonary arterial circulation.

A feature of the invention is that the tagged formulation such as a radiolabled formulation may be aerosolized directly from its container which is coated with a material such as lead to prevent or hinder the flow of radiation.

An advantage of the invention is that it exposes the patient and the caregiver to smaller amounts of radiation as compared to current methods.

Another advantage is that improved efficiency of delivery makes it possible to deliver 10 to 50 MBq of radioactive material (preferably 15 to 25 MBq and most preferably 20 MBq) to the lungs of a patient while using one or two small containers of radioactive material sealed with a radiation seal.

An object of the invention is to provide a container which holds radioactive formulation (e.g., radioactive DTPA) to be aerosolized, which container comprises a porous membrane which protrudes outward in a stationary state or on the application of force forming a convex surface when radioactive formulation is forced against and through the membrane.

Another object is to provide such a container with radioactive shielding such as a lead coating and/or lead package surrounding wherein "lead" includes polymeric, material impregnated with lead and alloys and materials generally used to provide radioactive shielding.

Another object is to provide a method for creating radioaerosols which comprises drawing air over a surface of a porous membrane in a channel and forcing radioactive formulation against the membrane so as to protrude the membrane through a flow boundary layer into faster moving air of the channel.

Another object of the invention is to provide a delivery device which creates aerosolized particles of a formulation comprised of radiolabelled compound in a carrier and adds energy to the particles in an amount sufficient to evaporate carrier and reduce total particle size.

Another object is to provide a radioactive formulation delivery device which includes a desiccator for drying air in a manner so as to remove water vapor and thereby provide consistent particle sizes even when the surrounding humidity varies.

Another object is to provide a method of radioactive particle delivery which heats the airflow into which an aerosol is released with the heating being varied based on ambient temperature and humidity thereby providing a radioaerosol of consistent particle size to a patient.

A feature of the invention is that radioactive material can be dispersed or dissolved in a liquid carrier such as water and dispersed to a patient as dry or substantially dry particles.

Another feature is that the package includes lead shielding.

Another feature of the invention is that the porous membrane has a convex surface or becomes convex because it is flexible and will protrude outward upon the application of force.

An advantage is that the radioactive formulation can be safely and conveniently handled.

Another advantage is that the aerosolized radioactive formulation is fully and evenly dispersed in the lung providing a gas-like distribution pattern.

Another advantage of the invention is that particles do not readily agglomerate because they are released from a convex porous membrane protruding into faster moving air drawn through a channel by a patient.

Another advantage of the invention is that particle size can be adjusted by adjusting the amount of energy added and thus the amount of evaporation obtained.

Another advantage is that the size of the particles delivered will be independent of the surrounding humidity.

These and other objects, advantages and features of the present invention will become apparent to those persons skilled in the art upon reading the present disclosure and reviewing the figures forming a part hereof.

DETAILED DESCRIPTION OF PREFERRED EMBODIMENTS

Figure 1:
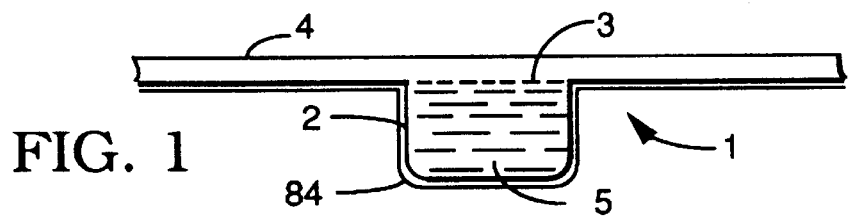
FIG. 1 is a cross-sectional view of a container of the invention.
Figure 2:
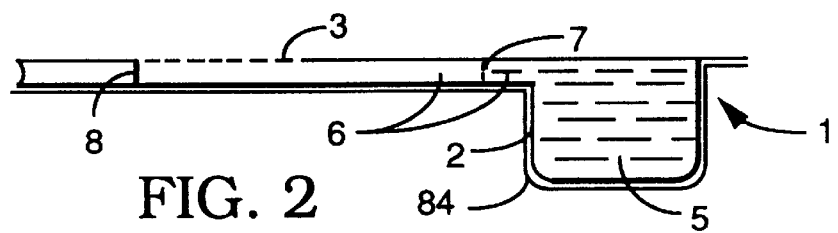
FIG. 2 is a cross-sectional view of a preferred embodiment of a container of the invention.

Before the container, device and methodology of the present invention is described, it is to be understood that this invention is not limited to the particular radioactive formulations, containers, devices, systems, components, and methods described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a radioactive formulation" includes mixtures of different formulations reference to "an image" includes reference to several images which might be created and reference to "the method of diagnoses" includes reference to equivalent steps and methods known to those skilled in the art, and so forth. Although the invention is at times described in connection with specific radioactive materials and formulations it may be used with a wide range of radioactive materials and formulations.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

Definitions

The term "radioactive material" shall mean any radioactive compound or substance labelled as a radioactive compound which can be administered to the lungs of a human patient with an acceptable degree of safety, and that when deposited in the lung will emit sufficient radiation such that an image can be created showing the presence of the material in the lung. A preferred radioactive material is $^{99m}$Tc-labelled diethylene triamine pentaacetic acid (DTPA). Other material can be labelled with $^{99m}$Tc such as carbon particles and then placed in a liquid carrier, e.g., water, ethanol, or a mixture thereof.

The terms "tagged material," "labelled material" and the like are used interchangeably herein to mean any material which is itself or attached to a tag or label which is detectable by any means. Such a tagged or labelled material includes radioactive materials. However, tags and labels can also be in the form of dyes including fluorescent dyes or any compound which can be formulated and administered to the lungs of a human patient with an acceptable degree of safety, and when deposited in the lung will migrate into the circulatory system of a human patient and be detectable within the circulatory system quantitatively.

The term "radioactive aerosol" is intended to encompass aerosolized radioactive materials, which materials are generally in the form of a small particles having a size and a range of 0.5 to 10 microns, more preferably 1.0 to 3.0 microns. Although an aerosol may contain some gas (e.g., due to evaporation), the term is not intended to encompass a pure gas, i.e., the form of a radioactive material wherein all of the particles are molecular in size.

The term "perfusion image" and/or "Q-scan" means an image created on a recording medium of any sort which image is the result of exposure to radioactive particles emitted from the pulmonary arterial circulation after injection of radioactive particles into the circulation.

The term "ventilation image" and "V-scan" means an image created on any medium as a result of radiation striking any recording medium wherein the radiation is emitted from radioactive particles inhaled into the lungs of a patient.

The term "velocity of particles" shall mean the average speed of particles of radioactive formulation moving from a release point such as a porous membrane or a valve to a patient's mouth.

The term "bulk flow rate" shall mean the average velocity at which air moves through a channel considering that the flow rate is at a maximum in the center of the channel and at a minimum at the inner surface of the channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate.

The term "delivery event" shall be interpreted to mean the administration of a radioactive aerosol to a patient by the intrapulmonary route of administration which event involves the release of radioactive aerosolized particles into the inspiratory flow path of a patient. Accordingly, a delivery event may include the release of radioactive formulation contained within one or more containers. A delivery event is not interrupted by a monitoring event which would indicate, if followed by further radioactive formulation delivery, the beginning of a new delivery event. A dosing event will involve the delivery of a sufficient amount of radioactive material to the lung of a patient such that, when in the lung, the material releases enough radioactivity so as to create an image.

The term "carrier" shall mean a liquid, flowable, pharmaceutically acceptable excipient material in which a radioactive material is suspended in or dissolved in. Useful carriers do not adversely interact with the radioactive material and have properties which allow for the formation of aerosolized particles preferably particles having a diameter in the range of 0.5 to 12.0 microns when a formulation comprising the carrier is forced through pores having a diameter of 0.25 to 6.0 microns. Preferred carriers include water, ethanol and mixtures thereof. Other carriers can be used provided that they can be formulated to create a suitable aerosol and do not adversely effect the radioactive material or human lung tissue.

The term "measuring" describes an event whereby either the inspiratory flow rate or inspiratory volume of the patient is measured in order to determine an optimal point in the inspiratory cycle at which to release aerosolized radioactive formulation. An actual measurement of both rate and volume may be made or the rate can be directly measured and the volume calculated based on the measured rate. It is also preferable to continue measuring inspiratory flow during and after any delivery of radioactive material and to record inspiratory flow rate and volume before, during and after the release of radioactive aerosol. Such reading makes it possible to determine if radioactive material was properly delivered to the patient.

The term "monitoring" event shall mean measuring lung functions such as inspiratory flow rate, and/or inspiratory volume so that a patient's lung function as defined herein, can be evaluated before and/or after delivery of radioactive material, thereby making it possible to evaluate any effect delivery might have and advise the caregiver as to the patient's lung function.

The term "inspiratory flow rate" shall mean a value of air flow calculated based on the speed of the air passing a given point in a measuring device. Measurements are preferably carried out at atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data. Measurements are preferably carried out at atmospheric pressure, ±5% and temperature in the range of about 10° C. to about 40° C.

The term "inspiratory flow profile" shall be interpreted to mean data calculated in one or more events measuring inspiratory flow and cumulative volume, which profile can be used to determine a point within a patient's inspiratory cycle which is optimal for the release of radioactive formulation to be delivered to a patient. An optimal point within the inspiratory cycle for the release of radioactive formulation is based, in part, on a point within the inspiratory cycle likely to result in the maximum delivery of radioactive formulation and based, in part, on a point in the cycle most likely to result in the delivery of an even gas-like distribution of radioactive particles. Obtaining uniform gas-like distribution is the primary criterion and maximizing the amount delivered is an important but secondary criterion. Thus, a large number of different release points might be selected and provide for even distribution provided the selected point results in even distribution. To ensure even distribution and maximum delivery of radioactive material, the point is selected within given parameters.

The terms "formulation" and "liquid formulation" and the like are used interchangeably herein to describe any radioactive material with a pharmaceutically acceptable carrier in flowable liquid form having properties such that it can be aerosolized to particles having a diameter of 0.5 to 12.0 microns, preferably 1–3 microns. Such formulations are preferably solutions, e.g. aqueous solutions, ethanolic solutions, aqueous/ethanolic solutions, saline solutions and colloidal suspensions.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Quantitative determination of pulmonary function is important because lung disease is typically associated with deteriorating pulmonary function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out delivery of radioactive material in a delivery event and monitoring lung function in a monitoring event. A series of such events may be carried out and repeated over time to deliver the desired amount of radioactive material.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The term "substantially dry" shall mean that particles of radioactive formulation include an amount of carrier (e.g. water or ethanol) which is equal to (in weight) or less than the amount of radioactive material in the particle.

The term "respiratory disease" shall be interpreted to mean any pulmonary disease or impairment of lung function. Such diseases include restrictive and obstructive disease and diseases such as emphysema which involve abnormal distension of the lung frequently accompanied by impairment of heart action. Restrictive diseases tend to limit the total volume of air that a patient is able to exchange through inspiration and expiration. Restrictive disease, such as can be present in certain types of fibrotic processes, can therefore be detected by reduced FVC indices. Obstructive disease, such as is present in patients with asthma, tends not to affect the total volume of air exchangeable through inspiration and expiration but rather the amount of time required for forced exhalation of air. In particular, the $FEV_1$ is markedly reduced in patients with acute asthma symptoms. More specifically, the $FEV_1$, when taken as a ratio of FVC (i.e. $FEV_1$ divided by FVC), is markedly reduced in patients with acute asthma. In addition to increasing the amount of time required for a full forced expiration, the presence of acute bronchoconstrictive disease tends to decrease the peak expiratory flow measured over a typical forced exhalation. The respiratory disease may block the ventilation of a section of the lung and thereby prevent radioactive material from depositing in that area of the lung. In most situations the same area of the lung would receive blood. Accordingly, a comparison of a ventilation image with a perfusion image would indicate to the caregiver that the patient did not have a pulmonary embolism, but rather a blockage and/or restriction of air flow problem.

The terms "aerosolized particles" and "aerosolized particles of formulation" shall mean particles of formulation comprised of radioactive material and/or radiolabled material and carrier which are formed upon forcing a radioactive formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs. Preferably, the particles have a size in the range of 0.5 micron to about 12 microns (more preferably 1 to 3 microns) having been created by being forced through the pores of a flexible porous membrane which pores have a diameter in the range of about 0.25 micron to about 6.0 microns (preferably 0.5 to 1.5 microns) —the pores being present on the membrane in an amount of about ten to 10,000 pores over an area in size of from about 1 sq. millimeter to about 1 sq. centimeter. Preferred membranes have more than 10 pores and preferably more than 100 pores over 1 sq. cm. or less.

Components of Invention

Devices, packaging and methodology for creating aerosols are provided which allow for efficient and repeatable delivery of tagged materials and in particular radioaerosols to the lungs of a patient. Devices may be plug-in units or hand-held, self-contained units which are automatically actuated at the same release point in a patient's inspiratory flow cycle. The release point is automatically determined either mechanically or, more preferably calculated by a microprocessor which receives data from a sensor making it possible to determine inspiratory flow rate and inspiratory volume. The device is loaded with a single container or a cassette comprised of an outer housing which holds a package of individual collapsible containers of a tagged formulation which is preferably radioactive formulation such as $^{99m}$Tc-labelled diethylene-triamine pentaacetic acid (DTPA). Actuation of the device forces the radioactive formulation through a porous membrane of the container which membrane has pores (preferably more than 10) having a diameter in the range of about 0.25 to 6.0 microns. The container includes radioactive shielding in the form of a lead coating and/or a lead surrounding packet. The porous membrane is positioned in alignment with a surface of a channel through which a patient inhales air. The flow profile of air moving through the channel is such that the flow at the surface of the channel is less than the flow rate at the center of the channel. The membrane is designed so that it protruded outward at all times or made flexible so that when radioactive formulation is forced against and through the membrane the flexible membrane protrudes outward beyond the flow boundary layer of the channel into faster moving air. Because the membrane protrudes into the faster moving air of the channel the particles of aerosol formed are less likely to collide allowing for the formation of a fine aerosol mist with uniform particle size. To make an initial determination on the likelihood of an embolism the present invention does not require making and comparing two different types of images. Specifically, the invention does not require the use of conventional methodology whereby the radioactive material is deposited in the lung an image is recorded (ventilation image). To avoid the need for making an image a tagged material such as a radioactive formulation is delivered to the lungs of a patient and sufficient time is allowed to pass whereby the tagged material can diffuse into the circulatory system of the patient. A sample is then taken from the patient's circulatory system and compared with a known standard. If formulation is well distributed in the patient's lungs it will show up in the circulatory system in a known amount. If the amount detected in the circulatory system is low then it is likely the patient has a pulmonary embolism which is blocking circulation to an area of the lung.

Although the method described above can be used without making an image, in another embodiment an image of the lung is made after delivery of a radioactive material. Specifically, the radioactive material is delivered to the lung and a ventilation image is created by exposing the patient to a material sensitive to the radiation and thereby creating a ventilation image. A perfusion image of the lung is then taken by injecting radioactive formulation into pulmonary arterial circulation. The ventilation image (V) is compared with the perfusion image (Q). Thus, a (V/Q) mismatch indicates a particular type of pathophysiology such as a pulmonary embolism. Although the present invention does not require that the conventional methodology be followed, the container and device of the invention can be used in such procedures. See Nuclear Medicine in Clinical Diagnosis and Treatment. I. P. C. Murray, editor, published by Churchill Livingstone 1994 at Vol. 1, pages 29–46 and Vol. 2 at pages 1347–1356. See also An Atlas Of Clinincal Nuclear Medicine, Second Edition, I. Fogelman, M. N. Maisey and S. E. M. Clarke, published by Mosby, Martin Dunitz, 1994, Chapter 7, pages 521–575, incorporated by reference.

In one embodiment, after the aerosolized mist is released into the channel energy is actively added to the particles in an amount sufficient to evaporate carrier and thereby reduce particle size. The air drawn into the device is actively heated (to a temperature of from about 25° C. to about 50° C.) by moving the air through a heating material which material is pre-heated prior to the beginning of a patient's inhalation.

The amount of energy added can be adjusted depending on factors such as the desired particle size, the amount of the carrier to be evaporated, the water vapor content of the surrounding air and the composition of the carrier. In one embodiment the porous membrane is vibrated a frequency in the range of 575 to 17,000 kilohertz to aid in particle formation.

Particle diameter size is generally about twice the diameter of the pore from which the particle is extruded. In that it is technically difficult to make pores of 2.0 microns or less in diameter the use of evaporation can reduce particle size to 3.0 microns or less even with pore sizes well above 1.5 microns. Energy may be added in an amount sufficient to evaporate all or substantially all carrier and thereby provide particles of dry powdered radiolabled material or highly concentrated radiolabled material to a patient which particles are uniform in size regardless of the surrounding humidity and smaller due to the evaporation of the carrier. Air drawn into the device by the patient may be drawn through a desiccator containing a desiccant which removes moisture from the air thereby improving evaporation efficiency when the carrier is water.

General Diagnostic Methodology

Although the invention includes several aspects, its ultimate purpose is to provide information on which to diagnose a patient such as by placing a detectable label in the circulatory system or by providing clear readable images of the lung, which can be used in various types of diagnostic methodology. More specifically, the various devices, packaging, and methodology disclosed is directed towards delivering a uniform dispersion of aerosolized tagged particles to the airways of the lung, which particles are deposited uniformly throughout the lung. The particles delivered to the lung can then be detected within the patient's circulatory system and compared with a standard in order to make a diagnosis. Alternatively, the formulation delivered to the lung generates radioactivity which creates an image on an image recording device. That image is referred to as a ventilation image or V-scan in certain circumstance, and can be used to compare with a perfusion image, or Q-scan, when the diagnostic methodology is being carried out in order to determine if the patient has a pulmonary embolism.

Although the diagnostic methodology of the present invention can include the creation of a perfusion image, the essence of the invention relates to the particular manner in which the ventilation image is created. Ventilation images can be created by using a radioactive gas or radioactive aerosol. In terms of a quality of image created, a gas is preferred. However, images created using an aerosol are more desirable in terms of reduced expenses, convenience, and general availability of material. The present invention endeavors to create a gas-like even distribution of particles while providing for the convenience, reduced expense, and availability of aerosol delivery of radioactive particles. We have found that there are a number of factors which are involved in creating an even gas-like distribution of radioactive particles in the lungs. These factors are described below in the section entitled "Factors Effecting Delivery." When taking into consideration all or any of these factors, it is possible to greatly improve the delivery of aerosolized particles and achieve a delivery pattern which is substantially the same as the delivery pattern obtained using radioactive gas. Once an even gas-like distribution of radioactive particles is obtained, it is possible to obtain a clear and useful ventilation image by allowing the radioactivity in the deposited particles to activate a recording medium such as an electronic sensor array within a gamma camera. The exposed recording medium will provide an image of the lungs showing the area where the radioactive particles were deposited in the lungs. This is the ventilation image. Simply viewing the ventilation image by itself can have some utility. For example, it could show obstructions in certain areas of one lung or the other. However, the usefulness of the ventilation image is greatly improved when it can be compared with a perfusion image.

A perfusion image is created by injecting radioactive materials into the circulatory system. More particularly, perfusion scintigraphy of the lung is accomplished by microembolization of radionucleotide-labelled particles in the pulmonary arterial circulation. Particulate material embolization causes a minor obstruction to pulmonary arterial blood flow. However, this affect is minor and almost never of physiological significance. The number of particles which impact a particular volume of the lung is proportional to the pulmonary arterial blood flow to that region. Perfusion scintigraphy thus provides a visual presentation of the relative distribution of pulmonary blood flow at the time of the injection of the radioactive material.

In order to create a perfusion image it is typical to inject 74–148 MBq (2–4 mCi) of $^{99m}$Tc-labelled macroaggregated albumin (MAA). Typically, images are obtained in eight views of the thorax, which images include: anterior, posterior, right/left posterior, and anterior oblique, right and left lateral.

After appropriate perfusion and ventilation images are obtained, a comparison is made. Ventilation images are referred to as V-scans and perfusion images, which refer to flow are referred to by the letter "Q". Accordingly, a V/Q mismatch comparison can be made using both types of images. Abnormalities in the perfusion scan that are mismatched by zones of abnormal ventilation are less likely to represent a pulmonary embolism. However, mismatched abnormalities (reduced perfusion with normal ventilation) have a high correspondence with pulmonary embolisms, particularly in situations where the patient shows a normal radiograph.

The present invention is largely directed towards components and methodology involved in delivering an aerosol of tagged formulation to the lungs for detection in circulator systems or obtaining a ventilation image, and is specifically involved in obtaining an even gas-like distribution of aerosolized tagged particles (e.g., radioactive particles) in the lungs of the patient. If even, gas-like distribution of aerosolized particles can be obtained, the resulting ventilation image or tagged material detected in and measured in the circulation will provide more reliable information to the caregiver who is carrying out the diagnostic analysis. The following section provides further details regarding factors affecting delivery.

Factors Effecting Delivery

Improved efficiency of delivery and even gas-like distribution of radioactive particles is obtained by simultaneously taking into consideration a number of factors. One should adjust:

(1) the release point within a patient's inspiratory flow rate inside a range of about 0.10 to about 2.0 liters/second preferably about 0.2 to about 1.8 liters per sec. and more preferably 0.15 to 1.7 liters per sec;

(2) the release point within a patient's inspiratory volume of about 0.15 to about 2.0 liters preferably 0.15 to 0.8 liters and more preferably 0.15 to about 0.4 liters;

(3) particle size in a range of about 0.5 to 6 microns and more preferably 1.0 to about 3 microns;

(4) the concentration of the radioactive material in the carrier so as to obtain a desired amount of radiation e.g., 1,500 MBq to 2,500 MBq/ml;

(5) the amount of heat added to the air about 20 Joules to about 100 Joules and preferably 20 Joules to about 50 Joules per 10 $\mu$l of formulation;

(6) the relative volume of air added by patient inhalation per 10 $\mu$l of radioactive formulation at about 100 ml to 2 l and preferably about 200 ml to 1 liter for evaporation and without evaporation 50–750 ml preferably 200–400 ml;

(7) the rate of vibration of the porous membrane from 575 to 17,000 kilohertz;

(8) pore size to a range of about 0.25 to about 6.0 microns in diameter preferably 0.5 to 3 microns and more preferably 1–2 microns;

(9) viscosity of the radioactive formulation to a range of from about 25% to 1,000% of the viscosity of water;

(10) extrusion pressure in a range of about 50 to 600 psi and preferably 100 to 500 psi;

(11) ambient temperature to 15° C. to 30° C. and ambient pressure between 1 atmosphere and 75% of 1 atmosphere;

(12) the ratio of liquid carriers to each other to be consistent;

(13) maintain a constant ratio of carrier to radioactive material;

(14) the desiccator to maximize removal of water vapor from air;

(15) the shape of the pore opening to be circular in diameter and a conical in cross-section with the ratio of the diameter of the small to large end of the cone being about ½ to 1/10, and the shape of the porous membrane to an elongated oval;

(16) the thickness of the membrane to 5 to 200 microns; preferably 10–50 microns;

(17) the membrane to have a convex shape or to be flexible so that it protrudes outward in a convex shape beyond the flow boundary layer when formulation is forced through it; and

(18) the firing point to be at substantially the same point at each release for the parameters (1–17), i.e., each release of radioactive formulation is at substantially the same point so as to obtain repeatability of dosing.

Delivery with Disposable Container

Containers of the invention are considered disposable in that they are preferably brought into an aerosol release position within a device, subjected to pressure in order to discharge the contents through the porous membrane and then moved out of the aerosol release position after a single use and discarded. Reusing the containers is undesirable in that the porous membrane includes tiny pores which can be easily clogged which would interfere with repeatability in dosing. Further, reusing a container after the opened pores had been exposed to the atmosphere could cause contamination of the contents of the container. In the description put forth below the contents of the container is referred to as a radioactive formulation. This is done because a radioactive formulation is preferred and in one embodiment of the invention must be used. However, in other embodiments of the invention it is possible to use a formulation which is tagged or labelled with some detectable label which can be delivered to the lungs, brought into the circulatory system and detected quantitatively within the circulatory system. Thus, one aspect of the invention includes disposable containers which are filled with a tagged or labelled formulation which formulation is not radioactive formulation and wherein the container does not include radioactive shielding. In the preferred embodiments described below radioactive shielding is referred to as is the radioactive formulation.

FIG. 1 is a cross-sectional view of a container 1 of the invention which is shaped by a collapsible wall 2. The container 1 has an opening covered by a flexible porous membrane 3 which is covered by a removable layer 4. The membrane 3 may be rigid and protrude upward in a convex configuration away from the radioactive formulation 5. When the layer 4 is removed the wall 2 can be collapsed thereby forcing the formulation 5 against the flexible porous membrane 3 which will then protrude outward in a convex shape. The layer 4 and surrounding sublayer 84 are optionally present. However, due to the radioactive properties of the formulation 5 it is desirable that they are present and are in the form of a material such as lead, lead alloy, polymer impregnated with lead which provides shielding from nuclear radiation.

FIG. 2 is a cross-sectional view of a more preferred embodiment of a container 1 of the invention. The container is shaped by a collapsible wall 2 which is preferably coated with a nuclear radiation shielding such as a lead or radiation shielding sublayer 84. This view shows the removable layer 4 not present. The container 1 includes an opening which leads to an open channel 6 which channel 6 includes an abutment 7 which is broken upon the application of force created by formulation 5 being forced from the container. When the abutment 7 is broken the formulation 5 flows to an area adjacent to the flexible porous membrane 3 and is prevented from flowing further in the channel 6 by a non-breakable abutment 8.

The container 1 as shown in FIGS. 1 and 2 can be designed without the use of the shielding layer 84. However, when the shielding layer 84 is not present, it is desirable to include the entire container within a shielding packet 85 as shown in FIG. 7. The packet 85 is comprised of any material known to provide shielding from radiation such as lead material which is sealed around the entire edge 86. A packet such as the lead packet layer 85 shown in FIG. 7 could also be used to encompass an entire package as shown within FIG. 8.

FIG. 3 is a cross-sectional view of the container 1 of FIG. 2 in use without a layer 84. The wall 2 is being crushed by a mechanical component such as the piston 9 shown in FIG. 3. The piston may be driven by a spring, compressed gas, or a motor connected to gears which translate the electric motor's circle motion to linear motion. The radioactive formulation 5 is forced into the open channel 6 (breaking the abutment 7 shown in FIG. 2) and against and through the membrane 3 causing the membrane 3 to protrude outward into a convex configuration as shown in FIG. 3.

The piston 9 has been forced against the container wall 2 after a patient 10 begins inhalation in the direction of the arrow "I". The patient 10 inhales through the mouth from a tubular channel 11. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity right next to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate i.e., 50% or less than the bulk flow rate.

To allow air to flow freely through the channel 11 the upper surface of the flexible porous membrane 3 is substantially flush with (i.e., in substantially the same plane as) the inner surface of the channel 11. Thus, if the membrane 3 remained in place when the formulation 5 move through the pores the formulation would be released into the slow moving or substantially "dead air" below the boundary layer 13. However, the membrane 3 protrudes outward through the boundary layer 13 into the faster moving air. This is desirable in that it aids in avoiding the agglomulation of particles. More specifically, when formulation exits the pores the formulation naturally forms spherical particles. Those particles slow down due to the frictional resistance created by the air through which the particles must travel. The particles existing behind them can face reduced air friction because the preceding particle have moved the air aside. Thus later released particles catch up with and merge into the earlier released particles. This can cause a chain reaction resulting in the formation of large particles which can not be readily inhaled into the lung—e.g., the formation of particles having a diameter of more than about 12.0 microns.

Figure 3:
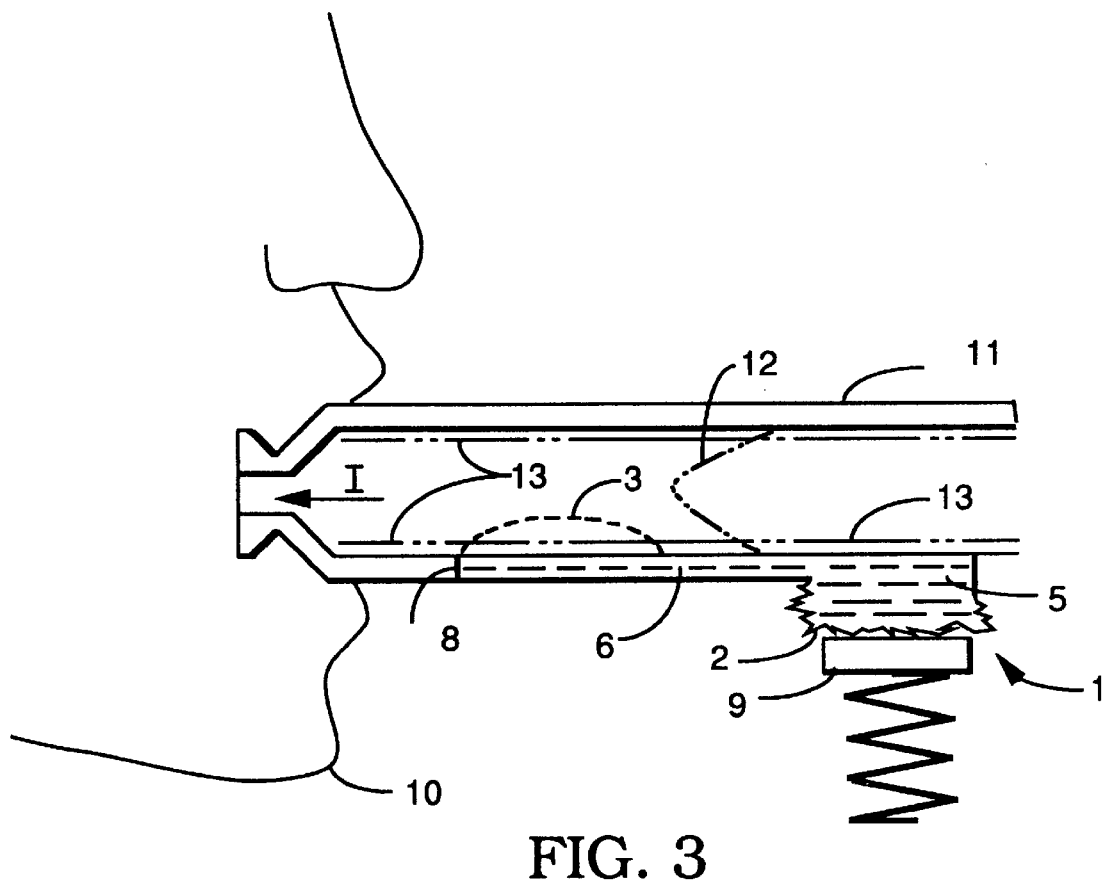
FIG. 3 is a cross-sectional view of the container of FIG. 2 in use in a channel of a radioactive formulation delivery device.
Figure 4:
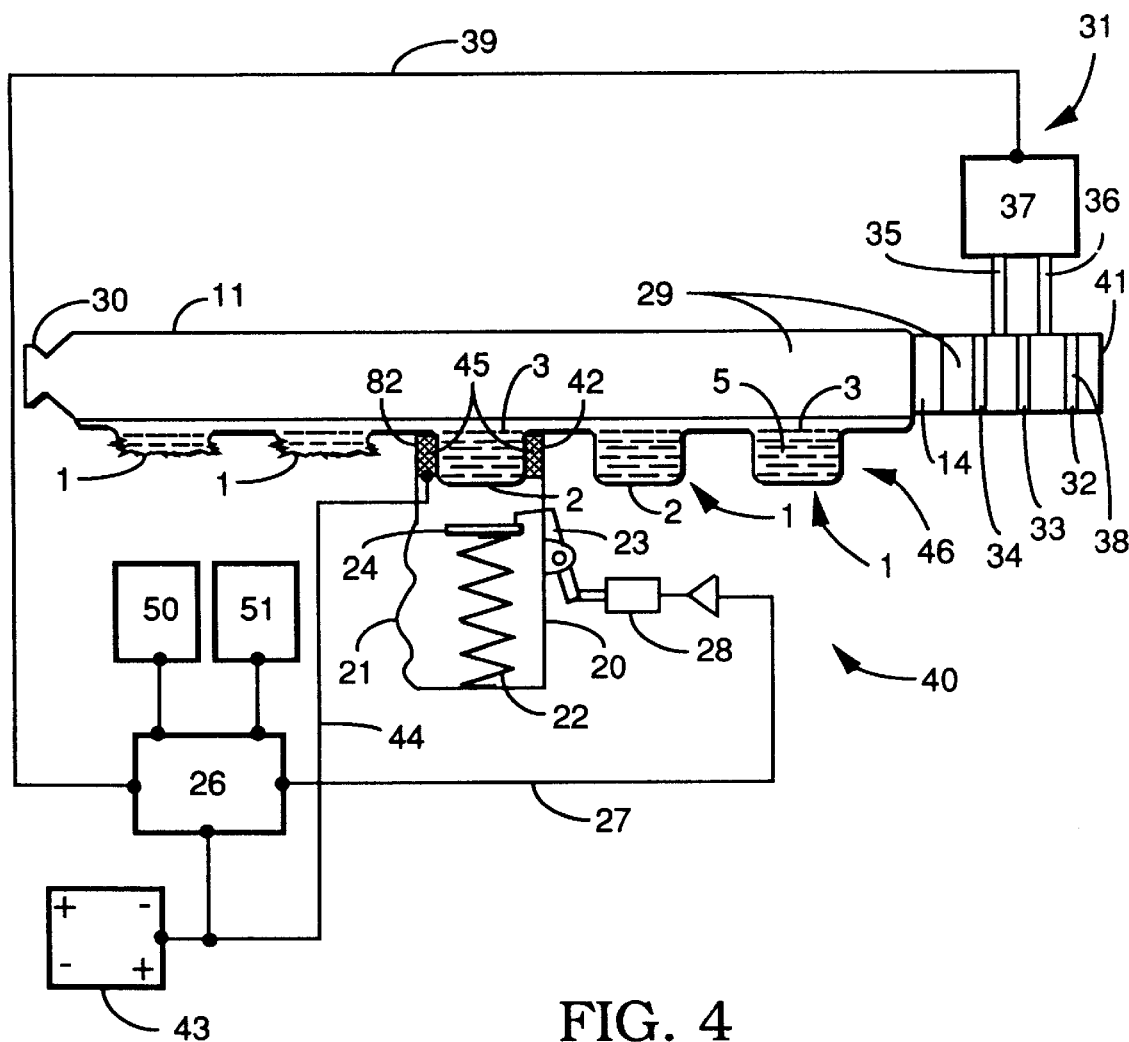
FIG. 4 is a plan view of a radioactive formulation delivery device of the invention.

A plan view of a simple embodiment of a radioactive material delivery device 40 of the present invention is shown within FIG. 4. The device 40 is loaded and operates with a strip of containers as shown in FIG. 4 or with a single disposable container shown in FIGS. 3 and 7. Before describing the details of the individual components of the device 40, a general description of the device and its operation is in order.

The background section discusses different ways in which ventilation imaging might be carried out. Some methods involve inhaling a radioactive gas, and others involve inhaling an aerosol created with a nebulizer. Conventional nebulizers suffer from a number of disadvantages. These disadvantages result in the inability to use these devices to provide a gas-like distribution of radioactive material to a patient. The disadvantages are due, in part, to the inability to (1) control particle size, (2) shield the patient and caregiver from radiation, (3) obtain release of aerosol in discrete dose at the desired point in the patient's respiratory cycle and efficiently deliver aerosolized material from discrete, radiation sealed containers. The present invention controls particle size by using a porous membrane with pores of a desired size, and by adding sufficient energy to the particles to evaporate carrier. This reduces particle size to a uniform minimum and reduces particle variability due to humidity variations. Further the dispensing device of the present invention preferably includes nuclear radiation shielding and electronic and/or mechanical components which eliminate direct user actuation releasing discrete pre-measured doses of radiation. More specifically, the device preferably includes a means for measuring inspiratory flow rate and inspiratory volume and sending an electrical signal as a result of the simultaneous measurement of both (so that radioactive aerosol can be released at a desired point each time) and also preferably includes a microprocessor which is programmed to receive, process, analyze and store the electrical signal of the means for measuring flow and upon receipt of signal values within appropriate limits sending an actuation signal to the mechanical means which causes radioactive aerosol to be extruded from the pores of the porous membrane.

The device 40 shown in FIG. 4 is loaded with a disposable package 46. To use the device 40 a patient (see FIG. 3) inhales air from the mouthpiece 30. The air drawn in through the opening 38 (and optionally the desiccator 41) flows through the flow path 29 of the channel 11. The disposable package 46 is comprised of a plurality of disposable containers 1. Each container 1 includes a formulation 5 of radioactive material and is covered by the porous membrane 3. An air-heating mechanism 14 located in the flow path 29. The air heating mechanism 14 is preferably positioned such that all or only a portion of the air flowing through the path 29 will pass by the heater, e.g., flow vent flaps can direct any desired portion of air through the heater 14. The heat is preferably turned on for 30 sec or less prior to inhalation and turned off after delivery to conserve power when the device is a hand-held battery powered device. This is not necessary for a plug-in type device.

The device 40 may be for stationary line powered use or be a hand-held, portable device which is comprised of (a) a device for holding a disposable package with at least one or a number of radioactive material containers, and (b) a mechanical mechanism for forcing the contents of a container (on the package) through a porous membrane. The device preferably further includes (c) a heating mechanism for adding energy to the air flow into which particles are released, (d) a monitor for analyzing the inspiratory flow of a patient, (e) a switch for automatically releasing or firing the mechanical means after the inspiratory flow rate and/or volume reaches a predetermined point (f) a means for measuring ambient temperature and humidity and (g) a source of power e.g., conventional batteries or plug-in to standard wall current.

The device for holding the disposable package may be nothing more than a narrow opening created between two outwardly extending bars 42 and 82 or may include additional components such as one or more wheels, sprockets or rollers notably mounted on the end(s) of such bars. The rollers may be spring mounted so as to provide constant pressure against the surface(s) of the package. The device may also include a transport mechanism which may include providing drive power to the roller(s) so that when they are rotated, they move the package from one container to the next. The power source 43 driving the roller(s) is programmed via the microprocessor 26 to rotate the rollers only enough to move the package 39 from one container 1 to the next. In order to use the device 40, the device 40 must be "loaded" i.e. connected to a package 39 which includes dosage units of radioactive material having liquid, flowable formulations of radioactive material therein. The entire device 40 may be self-contained, light weight (less than 1 kg preferably less than 0.5 kg loaded) and portable. The power source 43 is preferably in the form of standard alkaline batteries. Two 9 volt batteries could supply the heat required to heat the air which contacts the particles by about 20° C. for about 100 doses (see FIGS. 5 and 6 re energy required). Larger line powered units are also contemplated. Because of the radioactivity, smaller portable devices may be used for a single delivery event and then discarded, e.g., be produced as disposable units.

The radioactive formulation is preferably heated after the formulation has been forced through the pores of the membrane 3 and aerosolized i.e., energy is preferably added by heating the surrounding air by means of the air-heating mechanism 14 positioned anywhere within the flow path 29. The amount of energy added by the formulation heating mechanism (not shown and for non-portable embodiment) or air-heating mechanism 14 is controlled by the microprocessor 26 based on the amount of radioactive formulation in the container 1 and other factors such as the concentration of the radioactive material in the formulation and surrounding humidity. A hygrometer 50 and thermometer 51 are electrically connected to the microprocessor 26 allowing the amount of heat to be added to be adjusted based on ambient humidity and temperature.

Specific Radioactive Formulations

Different types of molecules require different strategies for the introduction of non-isotopic labels. Although $^{99m}$Tc can be used to "label" many substances ranging from simple ions (e.g., pyrophosphate) to complex molecules such as proteins, binding requires the presence of donor atoms arranged to form a chelating function. In the case of small molecules, complex formation usually nullifies the biological properties of the ligand because the positively charged metal ion will have a perturbing effect on the electron cloud of the ligand and higher order complexes (2:1 or 3:1 ligand-metal ratio) are likely to be formed. These factors will be pronounced in small complexes but may not affect the properties of larger peptides or proteins to such a marked extent unless the metal ion occupies active sites or a high metal-protein ratio is used.

To create formulations of the present invention any radioactive material can be used provided the radioactive material can be put into a formulation which formulation can provide aerosolized particles which can be inhaled by a patient and after inhalation will emit sufficient radiation that a readable image can be obtained. Although the radioactive material can be suspended in the formulation it is desirable to include soluble radioactive materials within a carrier and particularly desirable to include water soluble radioactive materials.

Typically, a radioactive material is contained on a support surface and is eluted off of the surface using a saline solution. More specifically, an anionic component of the radioactive material is eluted off of the surface when replaced with anions of a salt in solution. Accordingly, in a preferred embodiment molybdenum is on a solid surface and the molybdenum will naturally decay to technetium (Tc). When a normal saline solution is poured over the surface of the material an anion of $TcO^{-4}$ is eluted off the surface and into solution. The elution is only possible in the presence of anions such as chloride ions in the solution. For purposes of the present invention the concentration of the anion in the solution should be kept as low as possible while still maintaining the necessary rate of elution of the radioactive material off of the solid support. Thus, the solution poured over the solid support may have a salt concentration which is less than that of normal saline solution.

After the $TcO^{-4}$ anion is eluted into the aqueous saline solution the solution is generally treated further in order to slow its absorption into the body and eliminate a directed absorption towards particular cells. More specifically, $TcO^{-4}$ by itself can be absorbed so quickly that the desired image cannot be obtained. Further, the $TcO^{-4}$ tends to concentrate in certain cells such as those of the thyroid. To eliminate these problems the anion $TcO^{-4}$ is combined with diethylene triamine pentaacetic acid (DTPA) to form $^{99m}$Tc-labelled diethylene triamine pentaacetic acid.

The concentration of the radioactive material within the carrier will vary depending upon the radioactive material and carrier i.e., the solubility of the material in the carrier.

However, the object in formulating is not to obtain a particular concentration based on amount of radioactive material per unit of carrier but rather to obtain a formulation which contains a particular amount of radiation per unit volume of formulation. More particularly, the radioactive material is added to the formulation so as to obtain a formulation which has from about 1,500 MBq to about 2,500 MBq per milliliter of formulation. Most preferably, the formulation will include radiation in the amount of 2,000 MBq per milliliter of formulation ±20% MBq.

A particularly preferred formulation of the present invention does not include small amounts of extraneous material such as surfactants, and/or antibacterial agents. The isotope $^{99m}$Tc has a half life of only about six hours. Further, the solution containing the radioactive material can be treated in such a manner so as to eliminate the need for other components. By minimizing or not including additional components it is possible to use the solution to create particles which have a particular small size which is desirable in terms of obtaining a "gas-like" distribution of the particles in the lung. Thus, a particularly preferred formulation of the invention consists only of $^{99m}$Tc-labelled diethylene triamine pentaacetic acid in a saline solution. More specifically the saline solution will have a concentration of that of normal saline or less provided the concentration is sufficiently high to elute the $TcO^{-4}$ off of the substrate material.

Amount of Energy Added

Figure 5:
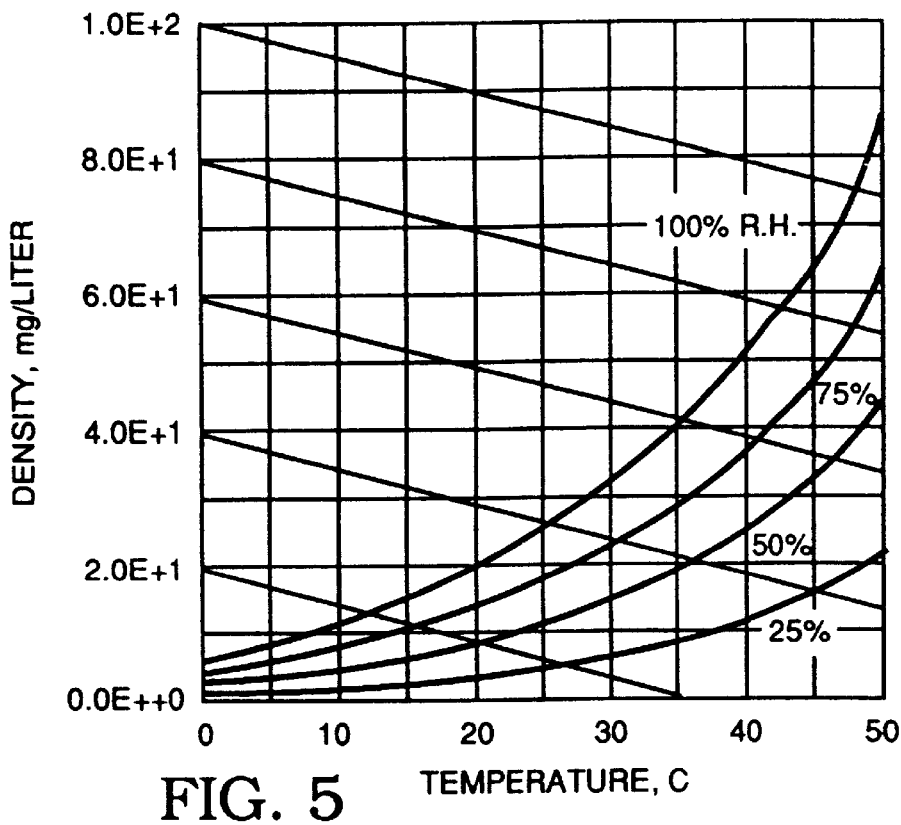
FIG. 5 is a graph plotting the density of water vapor in air versus temperature.

FIG. 5 is a graph which can be used in calculating the amount of energy needed to control the size of delivered droplets by controlling the amount of evaporation of carrier from the aerosolized droplets. The graph of FIG. 5 contains two types of information, the density of evaporated water vs. temperature and relative humidity, and the cooling of the air as the water evaporates. The four lines that show a rapid increase with temperature portray the density of water vapor in air, at 25, 50, 75, and 100% relative humidity. The 100% relative humidity curve represents the maximum number of milligrams of water that can be evaporated per liter of air. The diagonal lines show the temperature change of the air as the water droplets evaporate (hereafter called the air mass trajectory curves). As the evaporation proceeds, the density and temperature will change by moving parallel to these curves. To calculate these curves, air density of 1.185 grams/liter, air specific heat of 0.2401 calories/gram, and water latent heat of vaporization of 0.583 cal/mg were assumed. These values imply that a liter of air will cool 2 celsius degrees for every milligram of water evaporated, i.e. evaporating 10 micro-liters will cool a liter of air 20 celsius degrees.

FIG. 5 can be used to calculate the amount of preheating needed to evaporate all or substantially all of the carrier in the aerosolized particles. As an example, assume the initial ambient conditions are 25° C. and 50% relative humidity. Further, assume that one wants to evaporate 10 μl (10 mgs) of water from an aqueous solution of radioactive material. Finally, assume the final relative humidity is 75%. Under these conditions the aqueous carrier would not evaporate completely. More specifically, the final particles would contain approximately equal amounts of radioactive material and water. To calculate the amount of energy to add for this delivery manoeuver, refer to FIG. 5. Locate the point corresponding to 25° C. and 50% relative humidity. Move up by 10 milligrams, the amount of water to be evaporated. Now move to the left until the 75% RH curve is crossed. This occurs at about 29° C. These conditions (75% RH and 29° C.) represent the condition of the air as delivered to the patient. However, still more energy must be added to make up for the cooling of the air as the water evaporates. To calculate this amount of heat, move parallel to the air mass trajectory curves (downward and to the right) until the initial ambient water vapor density is reached, at approximately 47° C. Thus, sufficient heat to warm the air by 22° C. must be added to achieve near complete evaporation.

Figure 6:
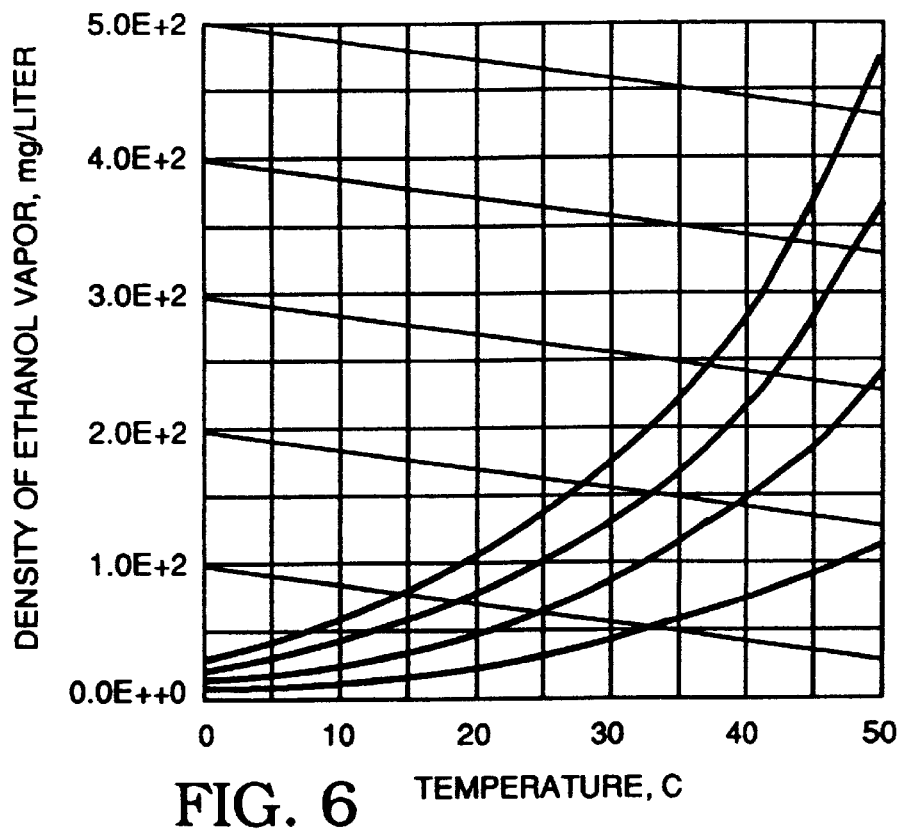
FIG. 6 is a graph plotting the density of ethanol vapor in air versus temperature.

FIG. 6 includes similar information with respect to ethanol which can be used in a similar manner. FIG. 5 shows the density of water vapor in air at 25°, 50° and 75° C. and 100% saturation with the air mass trajectory during evaporation also shown. The same is shown in FIG. 6 for the density of ethanol in air.

The evaporation and growth rates of aqueous droplets is a function of their initial diameter, the amount of radioactive material dissolved therein (concentration) and the ambient relative humidity. The determining factor is whether the water vapor concentration at the surface of the droplet is higher or lower than that of the surrounding air. Because the relative humidity at the surface of a particle (i.e. droplet of aerosolized formulation) is close to 100% for all the high concentration formulations, a five micron droplet will evaporate to a 1 micron dry particle in 0% humidity in less than 20 ms. However, if a particle of radioactive material 1 micron diameter is inhaled into the lungs (99.5% humidity) it will grow to about 3 microns in diameter in approximately one second by accumulating water from the humid lung environment.

The opening 38 may have a desiccator 41 positioned therein which desiccator includes a material which removes water vapor from air being drawn into the flow path 29. By reducing or more preferably eliminating water vapor from the air any water in particles of formulation can be more efficiently evaporated. Further, the particles delivered to the patient will have a smaller and more uniform size even if energy is not added to cause evaporation of water from the particles of the formulation.

The device may include a mouth piece 30 at the end of the flow path 29. The patient inhales from the mouth piece 30 which causes an inspiratory flow to be measured by flow sensor 31 within the flow path which path may be, and preferably is, in a non-linear flow-pressure relationship. This inspiratory flow causes an air flow transducer 37 to generate a signal. This signal is conveyed to a microprocessor which is able to convert, continuously, the signal from the transducer 37 in the inspiratory flow path 29 to a flow rate in liters per minute. The microprocessor 26 can further integrate this continuous air flow rate signal into a representation of cumulative inspiratory volume. At an appropriate point in the inspiratory cycle, the microprocessor can send a signal to send power from the power source 43 to the air-heating mechanism 14 which uses information from the hygrometer 50, thermometer 51 and particle size and amount of formulation. The microprocessor also sends a signal to an actuator which causes the mechanical means (e.g., the piston 24) to force radioactive formulation from a container of the package into the inspiratory flow path 29 of the device and ultimately into the patient's lungs. After being released, the radioactive material and carrier will pass through a porous membrane 3 to aerosolize the formulation and thereafter enter the lungs of the patient.

Figure 7:
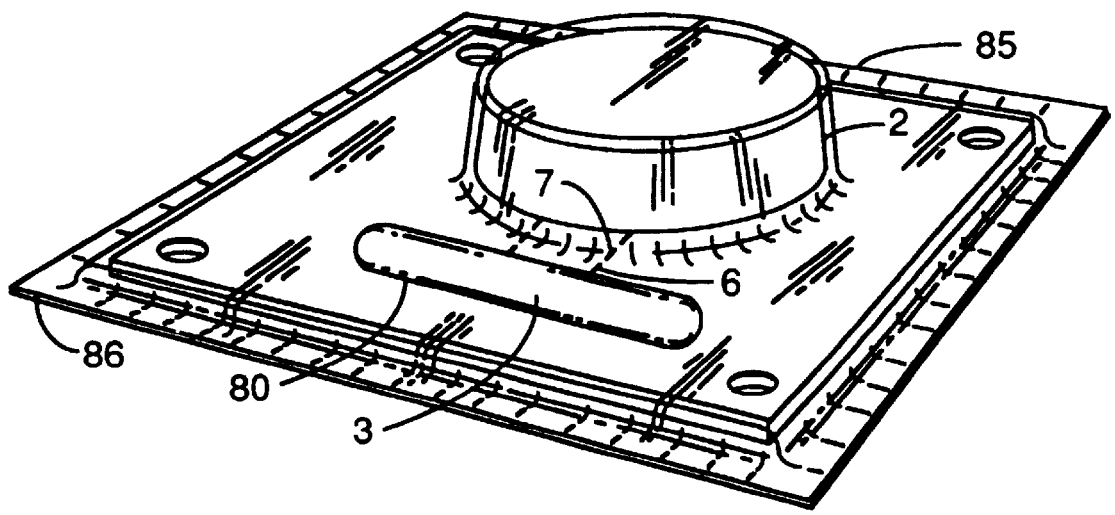
FIG. 7 is a perspective view of a lead shield packet of the invention which holds a container of the invention.
Figure 8:
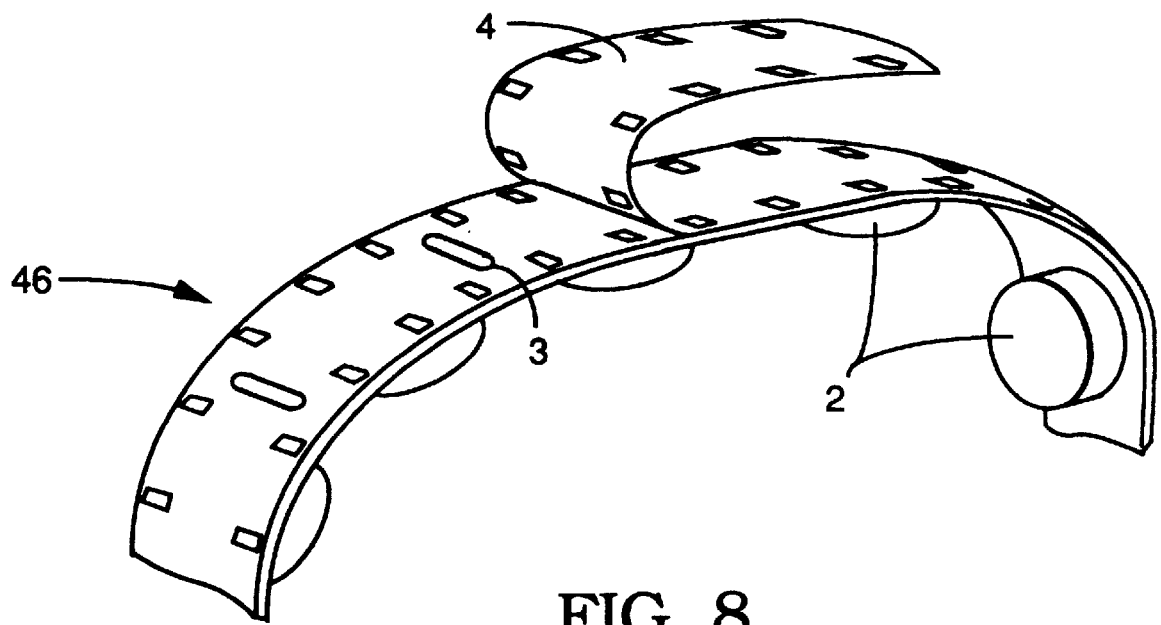
FIG. 8 is a perspective view of the package of the invention.

The convex shape of the membrane 3 plays an important role at this point. The membrane may be rigid and convex and a rigid convex membrane 80 is shown in FIG. 7. Alternatively, formulation 5 is forced from the container 1 by force applied from a source such as the piston or plate 24 causing the formulation 5 to press against a flexible membrane 3 causing it to convex outward beyond the plan of the resting surface of the membrane 3 and beyond the plan of the inner surface of the channel 11 which is aligned with the surface or membrane 3 when the container 1 is in a release position. The convex shape of the membrane 3 is shown in FIG. 3. The convex upward distortion of the membrane is important because it positions the pores of the membrane beyond the boundary layer 13 (shown in FIG. 3) into faster moving air of the channel 29. A number of containers may be connected together to form a package 46 as is shown in FIG. 8. The package 8 is in the form of an elongated tape but can be in any configuration, e.g., circular, square, rectangular, etc.

When pores of the membrane 3 are positioned beyond the boundary layer into the faster moving air of the channel advantages are obtained. Specifically, the (1) formulation exiting the pores is moved to an air stream where it can be readily carried to the patient and (2) the particles formed do not exit into slow moving or "dead" air and thus do not rapidly decelerate to a degree such that particles behind them catch up with, collide into and merge with the particle. Particle collisions are not desirable because they (a) result in particles which are too large and cannot be efficiently inhaled into the lung; and (b) result in an aerosol with diverse and unpredictable particle sizes. Either or both (a) and (b) can result in erratic dosing.

The air-heating mechanism 14 heats the surrounding air within the flow path 29. This causes carrier in the formulation to be evaporated more readily. If sufficient heat is added the only material reaching the patient is the substantially dry powder radioactive material with a particle size of 1 to 3 microns.

The methodology of the present invention could be carried out with a device that obtains power from a line powered source. However, the device is preferably a self-contained, hand-held device which is battery powered. Heating mechanisms of various types can be used. For example, see the heating mechanism in the self-contained, portable sealer for plastic colostomy bags in French patent 2,673,142 which is incorporated herein by reference. A portable heater is also taught in European patent applications 0,430,566 A2 for a "Flavor delivering article" and 0,358,002 for "Smoking articles utilizing electric energy," both of which are incorporated herein by reference to disclose and describe heating components powered by batteries.

When the formulation 5 includes water as all or part of the carrier it is also desirable to include a desiccator 41 within the flow path 29. The desiccator 41 is preferably located at the initial opening 38 but maybe located elsewhere in the flow path 29 prior to a point in the flow path when the formulation is fired into the flow path in the form of aerosolized particles. By drawing air through the desiccator 41 water vapor within the air is removed in part or completely. Therefore, only dried air is drawn into the remainder of a flow path. Since the air is completely dried water carrier within the aerosolized particles will more readily evaporate. This decreases the energy needs with respect to the heating devices 14. The desiccator material can be any compound which absorbs water vapor from air. For example, it may be a compound selected from the group consisting of $P_2O_5$, $Mg(ClO_4)$, $KOH$, $H_2SO_4$, $NaOH$, $CaO$, $CaCl_2$, $ZnCl_2$, and $CaSO_4$.

It is important to note that the firing threshold of the device is preferably not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of reproducibly delivering radioactive material in a gas-like delivery pattern.

The device preferably includes a means for recording a characterization of the inspiratory flow profile for the patient which is possible by including a microprocessor 26 in combination with a read/write memory means and a flow measurement transducer. By using such devices, it is possible to change the firing threshold at any time in response to an analysis of the patient's inspiratory flow profile, and it is also possible to record dosing events over time. In a particularly preferred embodiment the characterization of the inspiratory flow can be recorded onto a recording means on the disposable package.

FIG. 4 shows a cross-sectional plan view of a hand held, self-contained, portable, breath-actuated inhaler device 40 of the present invention. The device 40 is shown with a holder 20 having cylindrical side walls and a hand grip 21. The holder 20 is "loaded" in that it includes a container 1. A plurality of containers 1 (2 or more) are preferably linked together to form a package 46. Any of the components of the container or the device 40 may be coated with a material which provides a radiation shield, e.g., a lead coating.

The embodiment shown in FIG. 4 is a simple version of the invention. The device 40 may be manually actuated and loaded. More specifically, the spring 22 may be compressed by the user until it is forced down below the actuation mechanism 23. When the user pushes the actuation mechanism 23 the spring 22 is released and the mechanical means in the form of a plate 24 is forced upward against a wall 2 of a container 1. When the container 1 is compressed its contents are forced out through the membrane 3 and aerosolized. Two additional containers 1 shown to the left are unused. The device of FIG. 4 would not require the use of low boiling point propellants such as low boiling point fluorocarbons. However, the basic methodology of the present invention could be carried out by dispersing radioactive material in a low boiling point propellant and provide for formulation release using parameters as described herein.

It is important to note that a variety of devices can be used in order to carry out the methodology of the present invention. However, the device must be capable of aerosolizing radioactive formulation in a container and preferably does such forcing formulation through a porous membrane with the release point based on pre-programmed criteria which may be mechanically set or electronically set via criteria readable by the microprocessor 26. The details of the microprocessor 26 and the details of drug delivery devices which include a microprocessor and pressure transducer of the type used in connection with the present invention are described and disclosed within U.S. Pat. No. 5,404,871, issued Apr. 11, 1995, entitled "Delivery of Aerosol Medications for Inspiration" which patent is incorporated in its entirety herein by reference, and it is specifically incorporated in order to describe and disclose the microprocessor and program technology used therewith. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner. This is done to accommodate different radioactive formulations.

Microprocessor 26 sends signals via electrical connection 27 to electrical actuation device 28 which actuates the means 23 which fires the mechanical plate 24 forcing radioactive formulation in a container 1 to be aerosolized so that an amount of aerosolized radioactive material is delivered into the inspiratory flow path 29 when the flexible membrane 3 protrudes outward through the flow boundary layer. A signal is also sent to the heater 14 to add heat energy to the air in the flow path 29. The device 28 can be a solenoid, motor, or any device for converting electrical to mechanical energy. Further, microprocessor 26 keeps a record of all dosing times and amounts using a read/write non-volatile memory which is in turn readable by an external device. Alternatively, the device records the information onto an electronic or magnetic strip on the package 1. The recorded information can be read later by the care-giver to determine the effectiveness of the delivery of radioactive material. In order to allow for ease of use, it is possible to surround the inspiratory flow path 29 with a mouth piece 30.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 lpm and 800 lpm for exhalation. A variety of different types of flow sensors may be used as per U.S. Pat. No. 5,394,866, issued Mar. 7, 1995, U.S. Pat. No. 5,404,871, issued Apr. 11, 1995 and U.S. Pat. No. 5,450,336, issued Sep. 12, 1995, which are incorporated herein by reference. The flow sensor 31 includes screens 32, 33 and 34 which are positioned approximately ¼" apart from each other but may be comprised of a single screen or include a non-linear flow path. It is preferable to include the desiccator 41 at a point prior to the screens 32, 33 and 34 in the flow path so that the elimination of water vapor is considered in any measurement. Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 29, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 23 releasing the plate 24 which forces the release of formulation from a container 1 so that a controlled amount of radioactive formulation is delivered to the patient. The microprocessor 26 is optionally connected to an optionally present vibrating device 45 which may be activated.

Vibration Device

The vibration device 45 creates ultrasonic vibrations which are preferably at right angles to the plane of the membrane 3. The device 45 may be in the form of a piezoelectric ceramic crystal or other suitable vibration mechanism. A vibrating device 45 in the form of a piezoelectric crystal may be connected to the porous membrane by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 3 allowing for maximum use of the energy towards aerosolizing the liquid formulation 5. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 800 kilohertz (Khz) to about 4,000 kilohertz. The power output required depends upon the amount of liquid being nebulized per unit of time and the area and porosity of the membrane (generally comprised of a thin sheet of flexible polymeric plastic-like material).

Vibration is applied while the radioactive formulation 5 is being forced from the pores of the polycarbonate membrane 3. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about 50 to 600 psi, preferably 100 to 500 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores.

It is desirable to force formulation through the porous membrane with a relatively low pressure e.g., pressure less than 500 psi in that lower pressure reduces the chance of breaking the membrane during the release of formulation and makes it possible to make a thinner membrane. The thinner membranes make it easier to make small holes in that the holes or pores of the membrane are created using a focussed LASER. It is possible to reduce the pressure further by making the holes conical in cross-section. A LASER with a conical focus is used to burn holes through the membrane. The larger diameter of the conical shape is positioned next to the formulation and the smaller diameter opening is the opening through which the formulation ultimately flows. The ratio of the smaller opening to the diameter of the larger opening is in the range of about 1:2 to about 1:10 i.e., the larger opening is between 2 and 10 times the diameter of the smaller opening. By creating conical openings wherein the smaller end of the cone has a diameter of less than 6 microns it is possible to produce particles which have a diameter of less than 12 microns and it is also possible to force the formulation through the pores using a pressure of less than 500 psi. The small end of the conical opening preferably has a diameter of less than 3 microns for systemic delivery and less than 5 microns for pulmonary delivery and the pressure used for forcing formulation through the pores is preferable less than 350 psi.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol and ultimately obtaining a gas-like delivery of the radioactive material. To aid in avoiding the particle collision problem, it is possible to include a means by which air flow and the flexible membrane 3 prevent collisions. Specifically, the patient inhales thereby creating an air flow toward the patient over the protruding membrane 3. The air flow carries the formed particles along and aids in preventing their collision with each other. The shape of the container opening, the shape of the membrane covering that opening, as well as the positioning and angling of the flow of air through the channel 11 relative to the direction of formulation exiting the pores of the membrane 3 can be designed to aid in preventing particle collision. It is desirable to shape the container opening and matching membrane (i.e., the configuration of the pores on the membrane) so as to minimize the distance between any edge of the opening and the center of the opening. Accordingly, it is not desirable to form a circular opening (i.e., a circular configuration of pores) which would maximize the distance between the outer edges of the circle and the center of the circle, whereas it is desirable to form an elongated narrow rectangular opening (i.e., a configuration of pores) covered by a rigid membrane 80 as shown in FIG. 8. Using such a configuration makes it possible to better utilize the air flow relative to all of the particles of formulation being forced form the pores of the membrane 3. When a circular opening is used, particles which are towards the center of the circle may not be carried along by the air being drawn over the membrane 3 and will collide with each other. The elongated rectangle could be formed in a circle, thereby providing an annular opening and air could be forced outward from the outer and inner edges of the circle formed.

Operation of the Device 40

The device of FIG. 4 shows all of the components present within the single, hand-held, portable breath actuated device, e.g. the microprocessor 26 and flow sensor 31 used to provide the electronic breath actuated release of radioactive formulation. The device of FIG. 4 includes a holding means and mechanical means and preferably operates electronically, i.e. the actuation means is preferably not directly released by the user. The patient inhales through inspiratory flow path 29 which can form a mouth piece 30. Air enters the device via the opening 38. The inhaling is carried out in order to obtain a metering event using the differential pressure transducer 37. Further, when the inspiratory flow meets a threshold of a pre-programmed criteria, the microprocessor 26 sends a signal to an actuator release electrical mechanism 28 which actuates the mechanical means 23, thereby releasing a spring 22 and plate 24 or equivalent thereof, forcing aerosolized formulation into the channel 11, and out of the membrane 3 into the flow path 29 where the air surrounding the particles is optionally heated by the air heater 14. Further details regarding microprocessors 26 of FIG. 4 are described within U.S. Pat. No. 5,394,866, issued Mar. 7, 1995, entitled "An Automatic Aerosol Medication Delivery System and Methods", which is incorporated herein by reference in its entirety and specifically incorporated in order to describe and disclose flow measurements, the microprocessor and program technology used therewith.

Microprocessor 26 of FIG. 4 includes an external non-volatile read/write memory subsystem, peripheral devices to support this memory system, reset circuit, a clock oscillator, a data acquisition subsystem and a visual annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide (in a gas-like manner) controlled and repeatable amounts of respiratory radioactive material to a patient upon actuation. The microprocessor must have sufficient capacity to make calculations in real time. Adjustments can be made in the program so that when the patient's inspiratory flow profile is changed such is taken into consideration. This can be done by allowing the patient to inhale through the device as a test (monitoring event) in order to measure air flow with preferred radioactive material delivery points determined based on the results of several inhalations by each particular patient. This process can be readily repeated when the inspiratory flow profile is changed for whatever reason. When the patient's lung function has decreased the program will automatically back down in terms of the threshold levels required for release of radioactive formulation.

The present invention will result in a gas-like distribution of particles due to a number of features. Specifically, the membrane is permanently convex or is flexible and protrudes into fast moving air aiding the elimination of particle collisions. Further, the invention makes it possible to eliminate any carrier from the aerosolized particles and provide dry radioactive material particles to a patient which particles can be manufactured to have a uniform size. By delivering particles of uniform size repeatability of dosing is enhanced regardless of the surrounding environment, e.g. different humidity conditions. Still further, the device makes it possible to administer radioactive material at the same point with respect to inspiratory flow rate and inspiratory volume at each delivery point thereby providing gas-like delivery.

The method preferably uses a delivery device which is not directly actuated by the patient or caregiver in the sense that no button is pushed nor valve released by the patient or caregiver. On the contrary, the device of the invention provides that the actuation mechanism which causes radioactive formulation to be forced from a container which is fired automatically upon receipt of a signal from a microprocessor programmed to send a signal based upon data received from a monitoring device such as an airflow rate monitoring device. A patient using the device withdraws air from a mouthpiece and the inspiratory rate, and calculated inspiratory volume of the patient is measured simultaneously one or more times in a monitoring event which determines an optimal point in an inhalation cycle for the release of a dose of radioactive formulation. Inspiratory flow is preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of radioactive formulation with the preferred point being calculated based on the most likely point to result in a gas-like delivery of radioactive material in the lungs.

A flow rate monitoring device continually sends information to the microprocessor, and when the microprocessor determines that the optimal point in the respiratory cycle is reached, the microprocessor actuates a component which fires a mechanical means (and activates the vibration device) which causes radioactive formulation to be forced out of the container and aerosolized. Accordingly, radioactive material is repeatedly delivered at a pre-programmed place in the inspiratory flow profile of the particular patient which is selected specifically to maximize a gas-like delivery profile. It is pointed out that the device of the present invention can be used to, and actually does, improve the efficiency of delivery of radioactive formulation. However, this is not the most important feature. A more important feature is the release of a tightly controlled amount of radioactive formulation (with a narrow range of particle size) repeatedly at the same particular point in the respiratory cycle so as to assure the delivery of a controlled and repeatable amount of radioactive material to the lungs of each individual patient with a gas-like delivery profile with tightly controlled dosing.

The heating component(s) and/or the desiccator to remove water vapors aid in providing repeatability in dosing in that the particles reaching the patient will have the same size regardless of the surrounding humidity. By keeping the particle size the same at each dosing event the radioactive particles deposit uniformly throughout the lung at each event. These features improve repeatability along with automatic control of the release mechanism, combined with monitoring events in order to calculate the optimal flow rate and time for the release of radioactive formulation. Further, the radioactive particles will have uniform size in that all carrier is removed regardless of the humidity of the surrounding environment. Because the release mechanism is fired automatically and not manually, it can be predictably and repeatedly fired at that same point in the inspiratory cycle. Because dosing events are preferably preceded by monitoring events, the point in the inspiratory cycle of the release can be readjusted based on the particular condition of the patient. For example, patients suffering from asthma have a certain degree of pulmonary insufficiency which may change quickly and which must be considered. Changes in lung function will be taken into account in the monitoring event by the microprocessor which will readjust the point of release of the radioactive formulation in a manner calculated to provide for the administration of an amount of radioactive material to the patient presently needed by the patient to produce enough radiation to allow for making a clear readable image.

When administering radioactive material using the inhalation device of the present invention, the entire dosing event can involve the administration of anywhere from 5 to 200 $\mu$l of $^{99m}$Tc-DTPA, but more preferably involves the administration of approximately 50 to 100 $\mu$l of $^{99m}$Tc-DTPA or another water soluble radioactive material which results in a deposit of an equivalent amount of radiation generating material in the lung. The container will include the formulation having radioactive formulation therein in an amount sufficient to deliver to the lung about 2 to about 200 MBq of radiation, preferably about 35 to 65 MBq and most preferably about 50 MBq. Other radioactive isotopes which can be used to create radioactive material for use with the present invention include $^{111}$In, $^{113m}$In, and $^{67}$Ga.

The entire dosing event may involve several inhalations by the patient with each of the inhalations being provided with radioactive material from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver radioactive material with a given inhalation is not of great significance and will not seriously disturb the reproducibility of the dosing event. Further, since relatively small amounts are delivered with each inhalation, the patient can safely administer additional radioactive material without fear of overdosing.

A variety of different embodiments of the dispersion device of the invention are contemplated. In accordance with one embodiment it is necessary to carry out manual cocking of the device. This means that energy is stored such as by retracting a spring so that, for example, a piston can be positioned below the container which holds the radioactive material. In a similar manner a piston connected to a spring can be withdrawn so that when it is released it will force air through the air dispersion vents. Automatic cocking of forced storing systems for both the radioactive formulation and the air flow may be separate or in one unit. Further, one may be manual whereas the other may be done automatically. In accordance with one embodiment the device is cocked manually but fired automatically and electronically based on monitoring the patients inspiratory flow. The formulation may be physically moved through the porous membrane in a variety of different ways. Formulation may be forced through the membrane by a piston or, without applying force to the formulation, the membrane being vibrated at frequencies sufficient to create an aerosol.

The device 40 schematically shown within FIG. 4 can be specifically operated as follows. A container 1 is loaded into the device 6. The device is then armed meaning that the piston such as the spring-loaded piston 24 is cocked. Further, a container 1 of the package is moved into position and any cover such as the cover 4 of FIG. 1 is stripped off of the porous membrane 3. Thereafter, the patient withdraws air from the mouthpiece 30 and the patient's inhalation profile is developed using the microprocessor 26. After the inhalation profile is determined, the microprocessor calculates a point within the inhalation profile at which radioactive formulation should be released in order to maximize repeatability of the dosing, e.g. by plotting a curve of breath velocity versus time and determining the point on the curve most likely to provide a gas-like delivery profile. However, in order to carry out methodology in accordance with the present invention it is not necessary to plot any curve of breath velocity versus time. The device can be set so that the dose will be repeatedly released at approximately the same point with respect to inspiratory flow rate and inspiratory volume. If the device repeatedly fires at the same inspiratory flow rate and inspiratory volume each time the patient will receive substantially the same dose. Both criteria must be measured and used for firing to obtain repeatability.

The microprocessor of the present invention can be programmed to release radioactive formulation based on all or any of the following parameters.

(1) Delivery should be at an inspiratory flow rate inside a range of about 0.10 to about 2.0 liters per second (efficiency can be obtained by delivering at a flow rate in a range of 0.2 to about 1.8 liters per second and more preferably 0.15 to 1.7 liters per second). Repeatability of the delivery is obtained by releasing at substantially the same inspiratory flow rate at each release.

(2) Delivery should be at a point within a patient's inspiratory volume of about 0.15 to about 2.0 liters (further efficiency of delivery can be obtained by delivering within a range of 0.15 to 0.8 liters and more preferably 0.15 to about 0.4 liters). Repeatability of delivery is obtained by delivering at the same inspiratory volume at each release.

(3) Delivery is improved by providing a system which creates particles for delivery wherein the particles are in the range of about 0.5 to about 12.0 microns, preferably 0.5 to 6 microns and more preferably 0.5 to about 3 microns.

(4) It is desirable to have a water soluble radioactive material and to dissolve the material to obtain a concentration of the radioactive material in the carrier to obtain a desired amount of radiation—1,500 MBq to 2,500 MBq, preferably 1,750 to 2,250 MBq/ml. By maintaining the concentration of radioactive to carrier in this range it is possible to create particles which are somewhat larger than would be desirable for delivery but to reduce those particles in size by evaporation of carrier.

(5) Air drawn into the flow path of the aerosolized particles is heated by adding energy to each 10 $\mu$l of formulation in an amount of about 20 Joules to 100 Joules, more preferably 20 Joules to 50 Joules. The heated air aids in reducing the effect of humidity and evaporates carrier away from the particles thereby providing smaller particles for inhalation.

(6) Air is added to the aerosolized formulation by the patient drawing air into the aerosolized mist in an amount of about 100 milliliters to 2 liters per 10 microliters of aerosol formulation.

(7) Vibration may be created on the porous membrane in an amount 575 to 32,000, preferably 1,000 to 17,000 and more preferably 2,000 to 4,000 kilohertz.

(8) The pore size of the membrane is regulated within a range of 0.25 to about 6.0 microns, preferably 0.5 to 3 microns and more preferably 1 to 2 microns. This size refers to the diameter of the pore through which the formulation exits the membrane. The diameter of the opening into which the formulation flows may be 2 to 10 times that size in diameter thereby providing a conical configuration.

(9) The viscosity of the formulation affects the amount of pressure which needs to be applied to force the formulation through the pores and should be within the range of 25% to 1,000% the viscosity of water.

(10) The extrusion pressure is regulated within a range of 50 to 600 psi more preferably 100 to 500 psi. Lower pressures may be obtained by using the conical configuration for the pore size.

(11) The microprocessor should also be provided information regarding the ambient temperature and atmospheric pressure. The temperature is preferably close to room temperature i.e., within a range of 15° C. to 30° C. An atmospheric pressure is generally 1 atmosphere or slightly lower at higher altitudes, e.g., about 75% of 1 atmosphere.

(12) To provide for consistency in dosing the ratio of the carrier to radioactive material should be maintained constant.

(13) A desiccator is preferably used to remove water vapor from air drawn into the flow path by the patient.

(14) The pores are preferably placed in the porous membrane in an elongated oval or elongated rectangular configuration. By configuring the pores in this manner and drawing air perpendicularly over the narrower dimension of the configuration it is possible to reduce the amount of collisions between particles and thereby avoid particles collision resulting in accumulation.

(15) The thickness of the membrane is preferably regulated in the range of 5 to 200 microns or more preferably 10 to 50 microns. Thinner membranes are useful in that less pressure is required to force formulation through the membrane. The membrane has a tensile strength of 5,000 to 20,000, preferably 8,000 to 16,000 and more preferably 14,000 to 16,000 psi.

(16) The membrane is configured so as to have a convex configuration which protrudes into faster moving air created by the patient's inhalation or is designed to be flexible so that it will assume a convex configuration when formulation is forced through the membrane.

(17) After the microprocessor is provided information with respect to above parameters or measurements a release point is chosen the microprocessor will continually return to substantially the same firing point at each delivery so as to obtain repeatability of dosing.

After radioactive material has been delivered it is possible to discontinue any readings with respect to flow and/or volume. However, it is preferable to continue readings with respect to both criteria after radioactive material has been released. By continuing the readings the adequacy of each patient's particular delivery maneuver can be determined. All of the events are recorded by the microprocessor. The recorded information can be provided to the caregiver for analysis. For example, the caregiver can determine if the patient correctly carried out the inhalation maneuver in order to correctly delivery radioactive material and can determine if the image created is effected by the manner of delivery. If necessary, various adjustments can be made, such as in the release point, to obtain a particular desired result.

The instant invention is shown herein in what is considered to be the most practical and preferred embodiments. It is recognized, however, that departures may be made therefrom which are within the scope of the invention and that obvious modifications will occur to one skilled in the art upon reading this disclosure.

What is claimed is:

1. A disposable container for use in aerosolized delivery of radioactive material to the lungs, comprising:

a wall which is moved upon the application of force to reduce container volume;

an opening in the container which opening is covered at least in part by a porous membrane having more than ten pores with a diameter in the range of about 0.25 to about 6.0 microns;

a formulation comprised of a tagged material and a carrier which formulation is characterized by its ability to be detached via its tag and to form an aerosol of particles which can be inhaled into a patient's lungs when the formulation is moved through the pores of the membrane; and a layer of material which completely surrounds the container wherein the material is comprised of a material which blocks the flow of nuclear radiation from the radioactive material.

2. The container of claim 1, wherein the opening forms an open channel leading from the opening to a breakable seal beyond which is an area covered by the porous membrane and further wherein the membrane is sufficiently flexible to protrude outward in a convex configuration upon the application of force.

3. The container of claim 1, wherein the pores have a cross-sectional configuration with a small end opening of 0.25 to 6.0 microns in diameter and a large end opening of 2 to 10 times the diameter of the small end.

4. The container of claim 1, wherein the formulation consists of water soluble radioactive material and water.

5. A disposable container for use in aerosolized delivery of radioactive material to a patient's lungs, comprising:

a wall which is moved upon the application of force to reduce container volume;

a porous membrane covering an exit path from the container, the porous membrane having more than ten pores with a diameter in the range of about 0.25 to about 6.0 microns;

a formulation comprised of a radioactive material and a carrier which formulation is characterized by forming an aerosol of particles which are inhaled into a patient's lungs when the formulation is moved through the pores of the membrane; and a cover layer comprising a material which hinders the flow of nuclear radiation.

6. The container of claim 5, wherein the exit path leads to an open channel leading to a breakable seal beyond which is an area covered by the porous membrane.

7. A disposable package comprising a plurality of interconnected disposable containers as claimed in claim 5.

* * * * *